US005570692A

United States Patent [19]
Morinaga

[11] Patent Number: 5,570,692
[45] Date of Patent: Nov. 5, 1996

[54] ULTRASONIC DOPPLER BLOOD FLOW DETECTOR FOR HEMORRHOID ARTERY LIGATION

[75] Inventor: Kazumasa Morinaga, Fukuoka, Japan

[73] Assignee: Hayashi Denki Co. Ltd., Kawasaki, Japan

[21] Appl. No.: 444,905

[22] Filed: May 19, 1995

[51] Int. Cl.$^6$ .................................................... A61B 8/00
[52] U.S. Cl. ............................. 128/662.05; 128/661.09; 128/662.06
[58] Field of Search ................... 128/660.03, 661.08, 128/661.09, 662.01, 662.05, 662.06; 606/140, 139; 600/101, 102, 104, 103, 108, 160, 178

[56] References Cited

U.S. PATENT DOCUMENTS

| | | |
|---|---|---|
| 4,327,738 | 5/1982 | Green et al. . |
| 4,375,818 | 3/1983 | Suwaki et al. . |
| 4,462,408 | 7/1984 | Silverstein et al. . |
| 4,750,902 | 6/1988 | Wuchinich et al. . |
| 4,802,487 | 2/1989 | Martin et al. . |
| 4,880,011 | 11/1989 | Imade et al. . |
| 4,911,173 | 3/1990 | Terwilliger ............................ 128/662.06 |
| 4,936,307 | 6/1990 | Saito et al. . |
| 4,974,590 | 12/1990 | Saito . |
| 5,054,491 | 10/1991 | Saito et al. . |
| 5,131,393 | 7/1992 | Ishiguro et al. . |
| 5,158,563 | 10/1992 | Cosman ...................................... 606/140 |
| 5,251,611 | 10/1993 | Zehel et al. . |
| 5,320,630 | 6/1994 | Ahmed ........................................ 606/140 |

Primary Examiner—George Manuel
Attorney, Agent, or Firm—Kalish & Gilster

[57] ABSTRACT

An ultrasonic doppler blood flow detector used for hemorrhoid artery ligation having a hollow insertion cylinder which is enclosed at the distal end and open at the near end, and can be inserted through the anus; the cylinder has an ultrasound transducer in its interior wall, for detecting blood flow in the affected artery, and a ligation hole next to the transducer, through which the detected artery is ligated with ligation device, such as a curved needle or a wire for cautery.

13 Claims, 6 Drawing Sheets

000
ULTRASONIC DOPPLER BLOOD FLOW DETECTOR FOR HEMORRHOID ARTERY LIGATION

FIELD OF THE INVENTION

This invention relates to an ultrasonic blood flow detector and, more particularly, to an ultrasonic doppler blood flow detector for hemorrhoid artery ligation.

BACKGROUND OF THE INVENTION

There are numerous treatments for hemorrhoids, and the ligature resection surgery (the ligation of the artery and removal of hemorrhoids) is considered the best treatment for serious hemorrhoids. While the use of ligation surgery is effective, it is an extensive procedure involving many steps, such as an enema, anesthesia, opening of the anal region, artery palpation, and ligation. It requires hospitalization, surgical anesthesia, and recovery. It is characterized by post-operative patient discomfort.

Outpatient procedures without anesthesia include "Rubber band ligation" and "Infrared coagulation therapy". While these are effective there can be technical problems in determining and reaching the best treatment point.

The present invention provides an ultrasonic doppler blood flow detector for hemorrhoid artery ligation that combines precise identification and location of the ligation point via a rapid, minimally invasive procedure for outpatient use without anesthesia.

Two references that disclose medical devices using doppler flow detectors are U.S. Pat. Nos. 4,375,818 ('818 Patent) and 4,802,487 ('487 Patent). The '818 patent discloses an ultrasonic diagnostic system with an ultrasonic wave transmitting and receiving transducer which is rockably disposed within the distal end of a portion of an endoscope which is inserted into a coeliac cavity. The transducer emits ultrasonic wave from within the coeliac cavity and directs it toward internal tissues of a physical body, thereby enabling an ultrasonic tomographic image to be obtained. Although the insertion of this device into the rectum is disclosed, nothing is disclosed relating to hemorrhoids or their treatment.

The '487 Patent discloses an ultrasonic diagnostic system within an endoscope. The ultrasound probe is mounted at the end of a catheter which connects the probe to an ultrasonic imaging system. The system is used to diagnose the papilla of Vater to determine if an abnormal blood vessel could hemorrhage. It has also been used to locate arteries in ulcers. Likewise, it can be inserted into the rectum to diagnose Crohn's inflammatory bowel disease or ulcerative colitis. The system is often used to locate tumors for treatment. The '487 Patent fails to disclose the use of its system for the treatment of hemorrhoids.

SUMMARY OF THE INVENTION

The present invention is an ultrasonic doppler blood flow detector used for hemorrhoid artery ligation. The device involves a hollow insertion cylinder which is enclosed at the distal end and open at the near end, and can be inserted through the anus. The cylinder has an ultrasound transducer in its interior wall, for detecting blood flow in the affected artery, and a ligation hole next to the transducer, through which the detected artery is ligated with ligation device, such as a curved needle or a wire for cautery. The enclosed end of the tube can be illuminated with a small light which can be wired through the handle or powered with a battery. The transducer can be wired through the handle or use a battery as well.

DETAILED DESCRIPTION OF THE INVENTION

Figure 1:
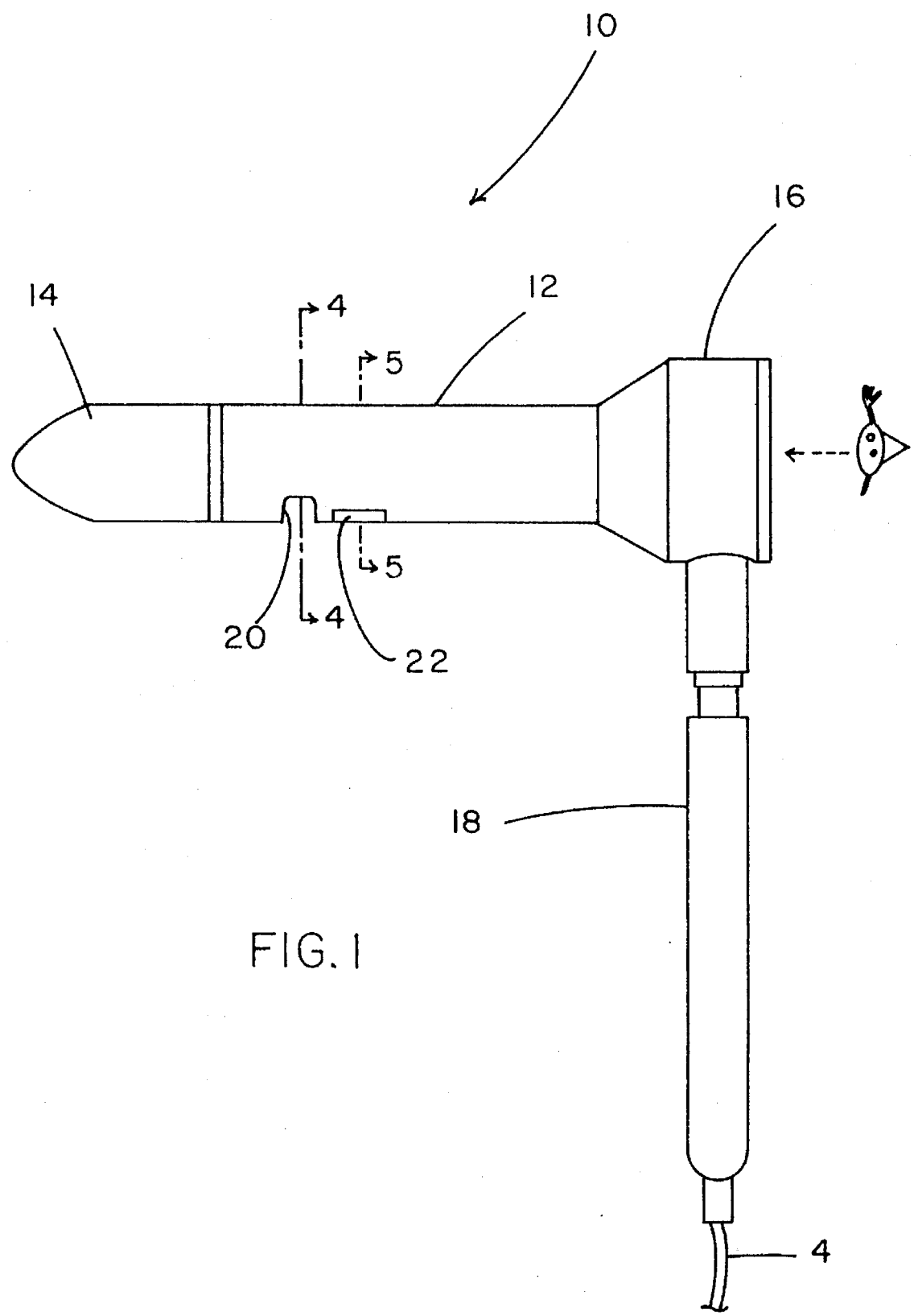
FIG. 1 is a side view of the probe of the detector.

FIG. 1 is a schematic representation of the side of the probe 10 of the ultrasonic doppler blood flow detector for hemorrhoid artery ligation of the present invention. The probe 10 has an insertion cylinder 12, which has an enclosed distal end 14 and an open near end 16. The distal end is optionally removable and is shaped for easy insertion. On the near end 16 of the cylinder 12 is, optionally, a view finder 24, which is shaped for easy viewing. Attached close to the near end 16 of the cylinder 12 is a handle 18 for handling and rotating the insertion cylinder 12 for ligation procedures.

On the cylinder 12 is a ligation hole 20 and an ultrasonic transducer 22 next to it, on the near end 16 side. To achieve a doppler effect, the transducer 22 is angled at an appropriate angle (about 60 degrees) to the hemorrhoid artery flow direction, between the distal end 14 to the near end 16. The length of the probe 10 from the distal end 14 to the near end 16 can range from about 3 to 7 inches. A preferred length is about 5.3 inches. The diameter of the probe can range from about 0.5 inch to about 1.5 inches. A preferred diameter is about 1 inch. The probe is constructed of a rigid or a flexible material, such as a metal, plastic or elastomer, that has a smooth surface and that can be sterilized.

Figure 2:
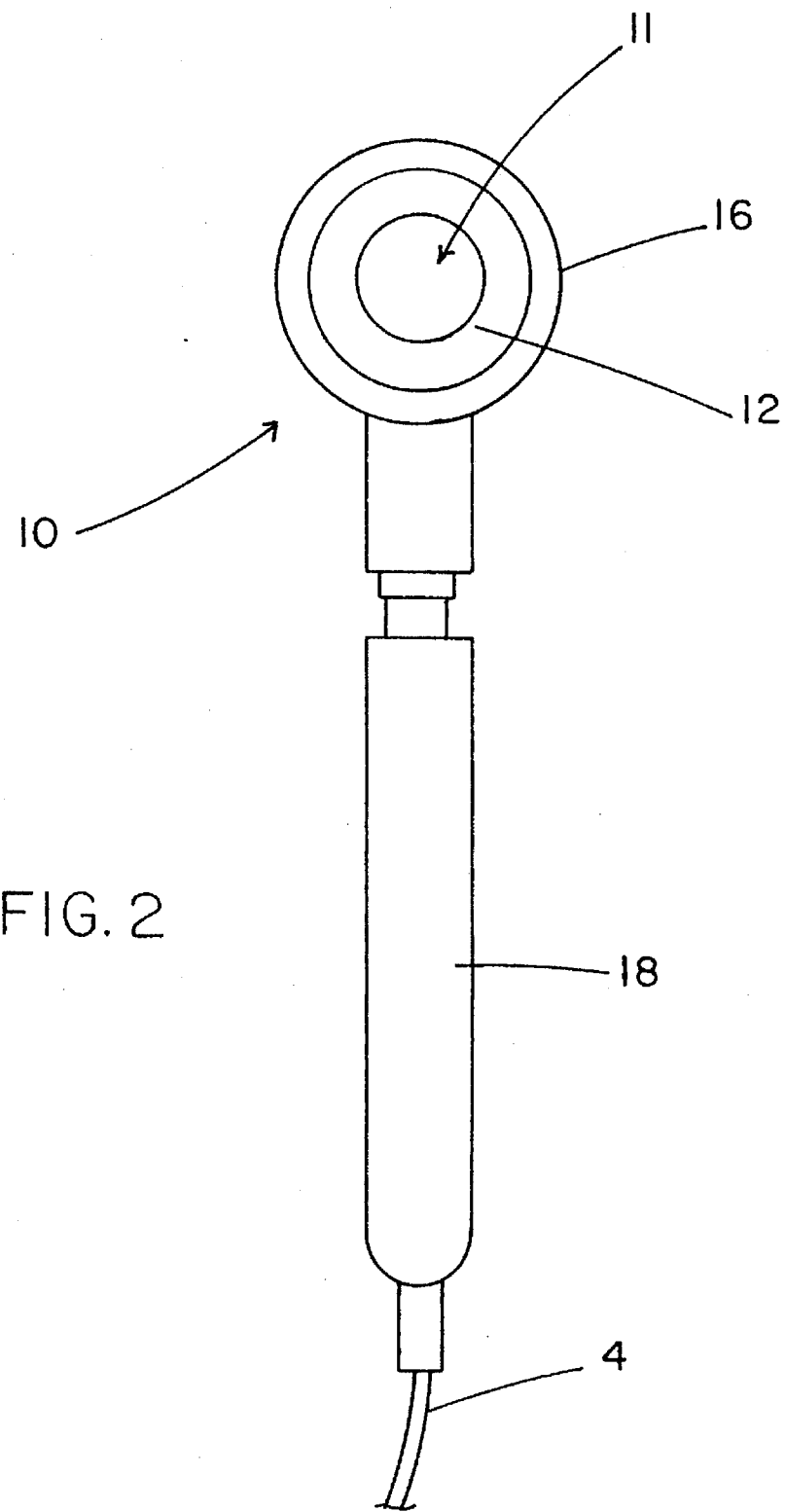
FIG. 2 is an end view of the probe of the detector.

FIG. 2 is an end view of the probe 10. The user of the probe can see the inside 11 of the cylinder 12 through the near end 16 of the cylinder. The handle 18 can be cylindrically shaped for easy handling.

Figure 3:
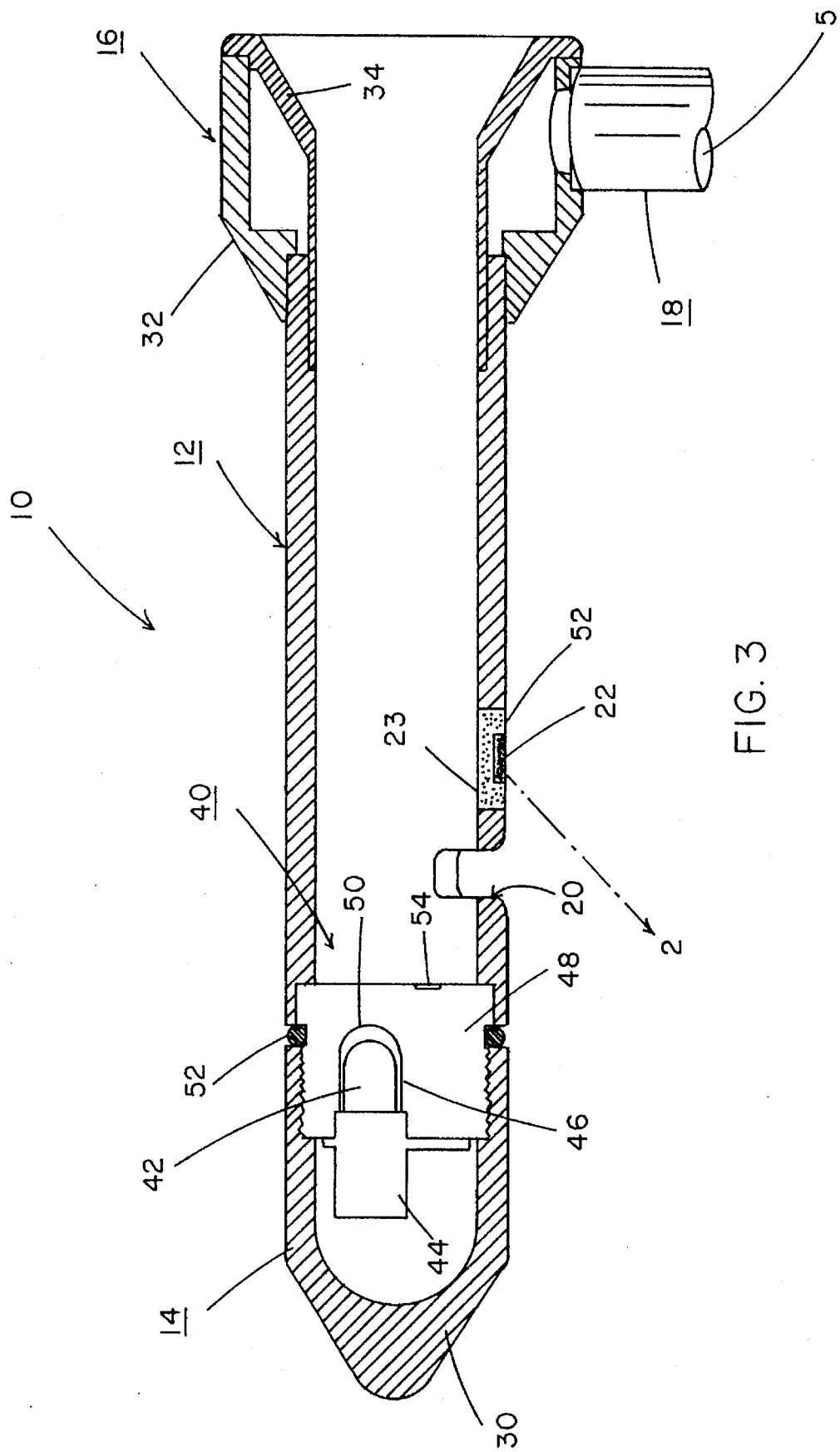
FIG. 3 is a magnified cross sectional view of the probe of the detector.

FIG. 3 is a magnified cross section of the probe of FIG. 1. The insertion cylinder 12 and the distal end 14 are preferably made of a clear plastic, such as polyethylene or acrylic resin for observation of the mucosa. The distal end 14 is tapered for easy insertion. The top 30 of the distal end is rounded. Optionally, as shown in FIGS. 1 and 3, the distal end 14 is removable for the replacement of the optional light bulb 42, which is inside the distal end 14. The light fixture 40 is made of the miniature bulb or light emitting diode (LED) 42, the bulb socket 44 and the light attachment 48. The bulb socket 44 is fixed in the light attachment 48 having a "U" hole 46.

The light attachment 48 optionally has a circular ligation guide inlet 54. The user places the top of the needle-holder holding the needle onto the left edge of the ligation guide inlet 54 and rotates approximately 90 degrees clockwise so that the needlepoint will go through the right edge of the ligation hole 20 for the first insertion into the mucosa. He moves the needle-holder along the guide to the right edge and rotates it until the needlepoint comes out of the mucosa so that the needlepoint will go through the left edge of the ligation hole 20 for suturing.

The light attachment 48 is fixed within the insertion cylinder 12 with fixing means such as an adhesive, snap-in or inset. The removable distal end 14 engages with the light attachment closeably by such means as screw threads, as shown in FIG. 3, with seals, gaskets or 0-rings. A rubber ring or gasket 56 provides a water-tight seal.

Figure 4:
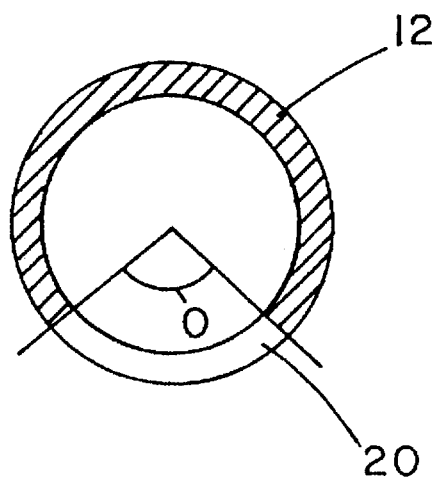
FIG. 4 is a cross section of line 4—4 in FIG. 1.

A shaded portion 50 of the "U" hole 46 blocks some of the light shining down the insertion cylinder 12, so that the user will not have the light shining directly in her eyes through the near end 16. The light attachment 48 is made of clear plastic, such as acrylic resin or polyethylene, so that the light shines through the entire attachment, providing ample illumination. The ligation hole 20 is a slit near the distal end 14 having an open angle O as shown in FIG. 4, which is a cross section at line 4—4 in FIG. 1. The size of the hole 20 is dependent on the size of the ligation means, such as a needle or wire for cautery. In FIG. 4, the width of the ligation hole 20 is ⅕ inch and its open angle O is about 90 degrees.

Figure 5:
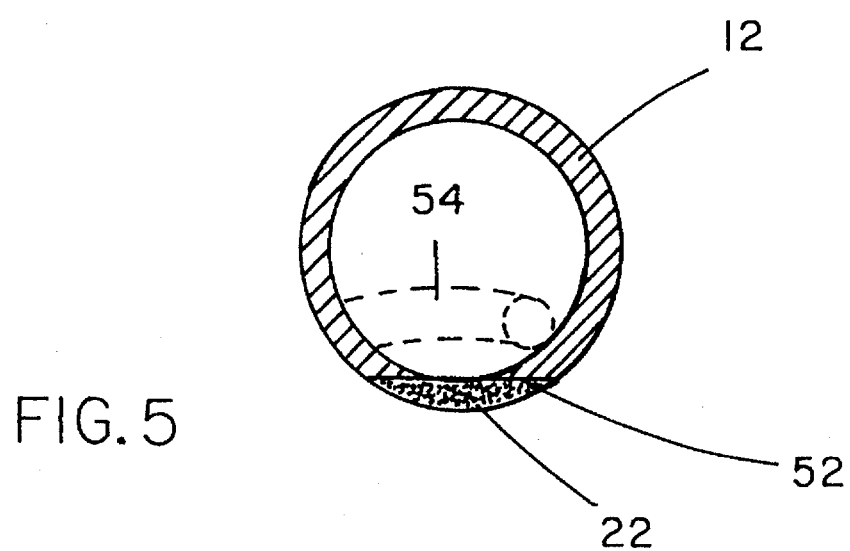
FIG. 5 is a cross section of line 5—5 in FIG. 1.

Next to the ligation hole 20 is the inlet 23 into which is inserted the molding plate 52 which contains the ultrasonic transducer 22. The ultrasonic transducer 22 is used to locate the hemorrhoid artery and to detect the cessation of sound after ligation on the extremity side of the artery. The transducer 22 can be either a continuous wave transducer or a pulsed wave transducer. The pulsed wave transducer is preferred because of its smaller size. The preferred frequency is approximately 8 mhz. The ultrasonic transducer 22 is angled at about 60 degrees to the hemorrhoid artery flow direction as arrow 2 in FIG. 3 shows. FIG. 5 is a cross section of line 5—5 from FIG. 1, showing how transducer 22 is placed in the insertion cylinder 12. The signal wire 4 for the transducer 22 and the power wire for the miniature light bulb 42 are wired in a through-hole 5 inside of the insertion cylinder 12 toward the handle 18 so that they won't obstruct the ligation.

Figure 6:
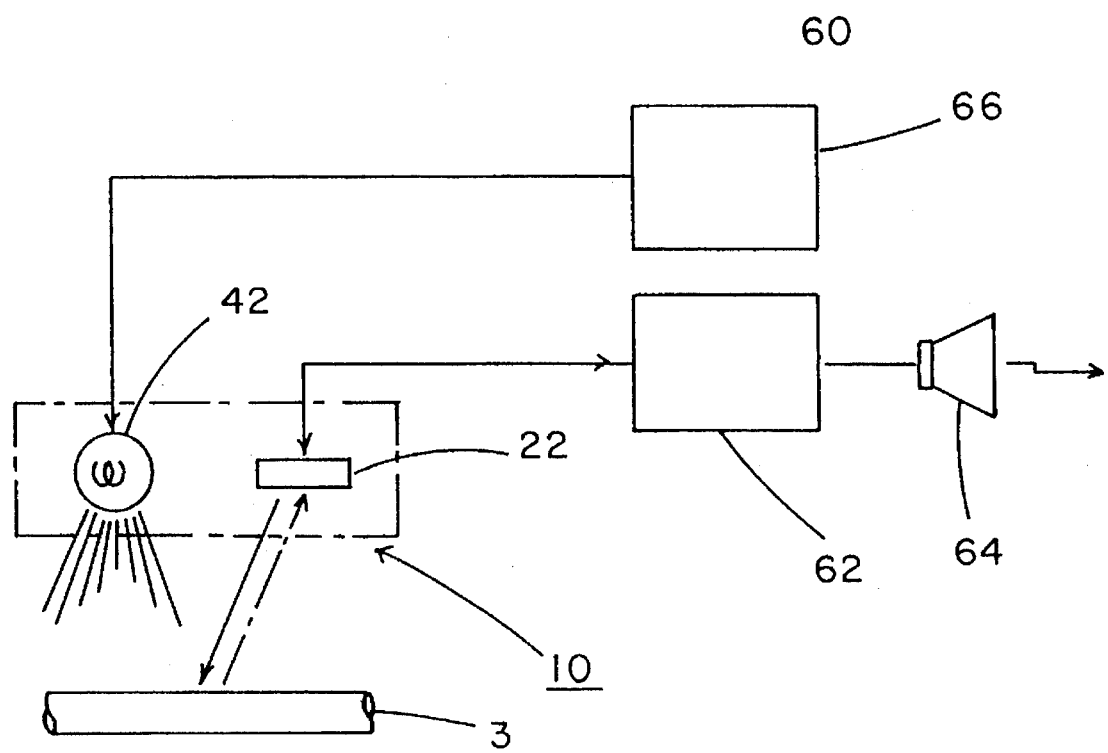
FIG. 6 is a block diagram of the detector.
Figure 7:
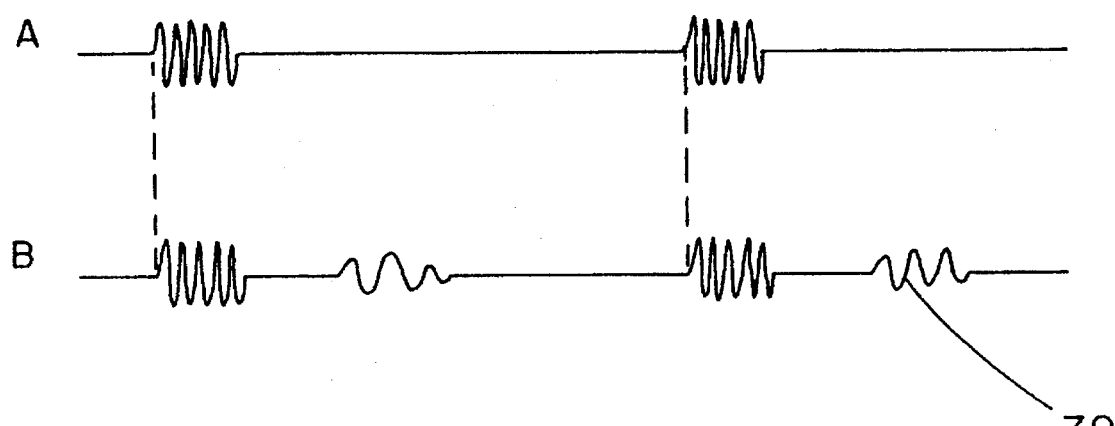
FIGS. 7A and B are scans of timing charts of doppler waveforms.

FIG. 6 is a block diagram of the ultrasonic doppler blood flow detector 60 for hemorrhoids artery 3 ligation of this invention. The transmitting and receiving circuits 62 supply the transmitting pulsed wave signals to ultrasound as FIG. 7A shows. The ultrasound is transmitted to external objects. The ultrasound moves straight through the biophysical object and is reflected by the moving object, i.e., the blood flow, as FIG. 7B shows. The transducer 22 converts the reflected ultrasound into electrical signals again. The transmitting and receiving circuits 62 amplify the converted signals and generate the hemorrhoid artery doppler sounds coming out from the speaker 64. The power supply circuits 66 are for the miniature bulb 42.

EXAMPLE OF THE INVENTION

The following is a procedure for using the claimed detector for hemorrhoid artery ligation:

1. The patient lies down on his side in a lateral position.
2. Ultrasonic gel is applied to the anal region and all over the insertion cylinder 12. Optionally, a local anesthetic gel, such as Xylokine Gel™, can be used, except in the area of the transducer 22.
3. The insertion cylinder 12 is inserted to the best depth for ligation of the artery, such that the ligation hole 20 is placed approximately 1 inch inside the dentate line.
4. The ultrasonic probe 10 is rotated slowly to locate the spot where the artery's doppler sounds are heard. The arteries are generally located at the 3, 7 and 11 o'clock positions. The left lateral position is used for the 3 o'clock arteries and the right lateral position is used for the 7 and 11 o'clock arteries.
5. The probe 10 is rotated slowly a second time to locate the point where the doppler sounds of the ligating artery are at the maximum so that the ligation hole 20 faces the ligation point, i.e., the hemorrhoid artery.
6. A ligation means, such as a curved needle or cautery wire, is inserted into the insertion cylinder 12 through the close end 16. The ligation means in inserted through the ligation hole 20 by rotating the needle toward the rectal ampulla. A thread insertion stick is used to insert a knot into the cylinder and to ligate the artery.
7. Ligation of the arteries is generally about 1 inch from the dentate line on the rectal ampulla, where there is an indolent area. The most serious of the hemorrhoids is ligated first. All of the 3 o'clock arteries can be ligated at one time. However, to minimize patient discomfort, the ligations should be performed separately in 2 or 3 surgeries on different days.
8. The artery can be located reliably using the doppler detector, even though the branch of the hemorrhoid artery is located on the upper side of the dentate line or there may be an abnormal route of the artery.
9. The artery should be monitored after ligation to be sure that the doppler sounds disappear.
10. Because the ligation occurs in indolent areas, there is no need for post-operative salve and suppositories.

Figure 8:
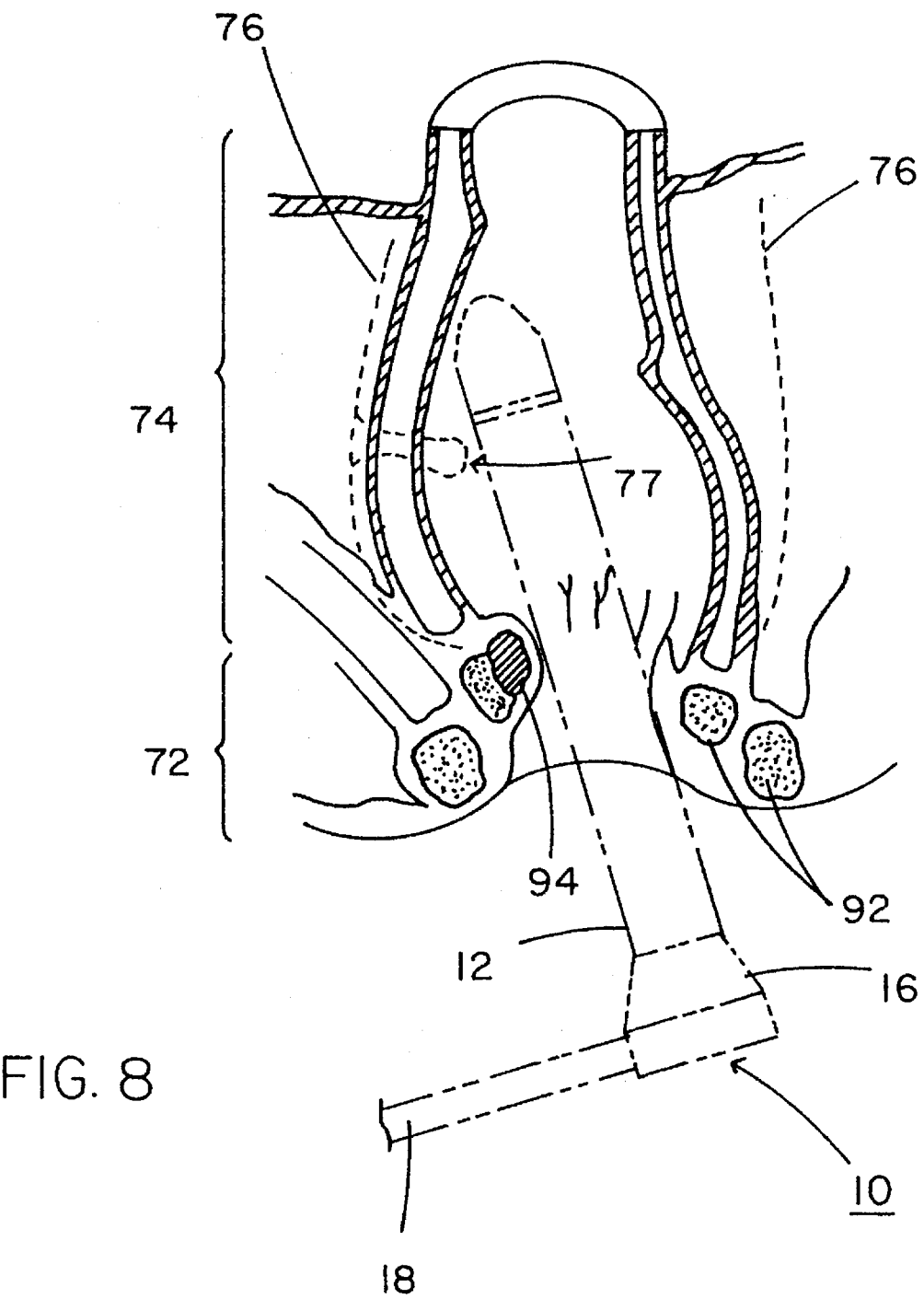
FIG. 8 is a cross section of an anal region with the probe inserted.

FIG. 8 shows a cross-section of an anal region with the probe 10 inserted. The probe 10 is inserted through the anal region 72 into the rectum area 74, past the anal sphincters 92 and the hemorrhoids 94. The hemorrhoid artery 76 forms a loop at the ligation spot 77, next to the probe 10.

The detector 60 can also be used for induration treatment of serious hemorrhoids as follows:

The ultrasonic probe 10 is pulled out, about 1 to 2 inches from the ligation point. The varicose vein forming the internal hemorrhoid will come into the insertion cylinder 12 through the ligation hole 20. The colored induration agent is injected into the varicose vein, which hardens, blocking the vein.

The advantages of this detector and the process of using it are:

The detector can be used in induration treatment.

The ligation can be done safely and reliably as an outpatient without anesthesia and pre-operative steps.

The surface of the insertion cylinder is made smooth for easy insertion into the anus. The shape, size and length of it are adequately selected so that the anus, mucosa and rectal tissue will not be scratched or damaged.

The probe 10 can be brightly lit for maximum visualization.

The insertion cylinder 12 and distal end 14 can be made of clear plastic, so the inside of the rectum and the hemorrhoid mucosa can be observed and diagnosed through the probe 10. A colored induration agent can be observed.

The ultrasonic transducer 22 is placed next to the ligation hole 20 toward the distal end, so the hemorrhoid artery can be easily detected and the success of the ligation can be determined upon the doppler sound cessation.

All the hemorrhoid arteries can be located by rotating the probe 10, after insertion, in one turn, so that all the arteries can be ligated on the same insertion, which shortens surgery time. Performing the surgery into two procedures, one on the right side of the patient, and one on the left side, will reduce patient discomfort.

The rapid, minimally invasive procedure reduces patient discomfort when treated as an outpatient.

I claim:

1. An ultrasonic doppler blood flow detector for use in ligation of hemorrhoid arteries of a patient, the detector comprising a hollow cylinder with an interior wall, which has a distal end and a near end, wherein the distal end is enclosed and the near end is open;

wherein the distal end of the detector is insertable through the patient's anus and along the rectal mucosa, and the near end is usable for viewing such rectal mucosa;

wherein the cylinder has an ultrasonic transducer in the interior wall for detecting blood flow in the artery; and wherein the cylinder has a ligation hole next to the transducer through which the artery is ligated with a ligation device.

2. The detector of claim 1, and further comprising a small light and light attachment means for fixing the small light therein to the detector in a position so that the distal end of the cylinder is illuminated with the small light.

3. The detector of claim 2, and further comprising a handle for holding the detector.

4. The detecor of claim 3, wherein the transducer is wired through the handle.

5. The detector of claim 3, and further comprising a light attachment having a U-hole in which the light is fixed, and having a ligation guide inlet.

6. The detector of claim 3, wherein the light is wired through the handle.

7. The detector of claim 1, wherein the distal end is tapered.

8. A method of ligating hemorrhoid arteries comprising (A) inserting: an ultrasonic doppler blood flow detector for use in hemorrhoid artery ligation comprising a hollow cylinder with an interior wall, which has a distal end and a near end, wherein the distal end is enclosed and the near end is open; wherein the cylinder has an ultrasonic transducer in the interior wall; and wherein the cylinder has a ligation hole next to the transducer; through the anus and along rectal mucosa;

(B) viewing the rectal mucosa through the near end of the detector;

(C) detecting blood flow through the artery with the ultrasonic transducer; and (D) ligating the artery with a ligation device through the ligation hole of the detector.

9. The method of claim 8, and further comprising illuminating the distal end of the cylinder with a small light.

10. The method of claim 9, and further comprising holding the detector by a handle, and powering the light by a wire through the handle.

11. The method of claim 10, and further comprising powering the transducer by a wire through the handle.

12. The method of claim 8, wherein the distal end is tapered.

13. The method of claim 10, and further comprising fixing the light in a U-hole in a light attachment which has a ligation guide inlet.

* * * * *